United States Patent [19]

Sarngadharan et al.

[11] Patent Number: 5,122,468
[45] Date of Patent: Jun. 16, 1992

[54] HUT-78 CELL LINES INFECTED WITH HTLV-III WHICH SECRETE GP160

[75] Inventors: Mangalasseril G. Sarngadharan, McLean, Va.; Vaniambadi S. Kalyanaraman, Germantown, Md.

[73] Assignee: Akzo N.V., Arnhem, Netherlands

[21] Appl. No.: 450,884

[22] Filed: Dec. 14, 1989

Related U.S. Application Data

[63] Continuation-in-part of Ser. No. 362,548, Jun. 7, 1989, which is a continuation of Ser. No. 232,859, Aug. 16, 1988, abandoned.

[51] Int. Cl.$^5$ ................................. C12N 5/10
[52] U.S. Cl. .................. 435/240.2; 435/70.4; 435/236; 435/5; 435/974
[58] Field of Search .............. 435/70.4, 240.2, 5, 435/236, 574; 530/395, 826

[56] References Cited

PUBLICATIONS

Rekosh et al. PNAS 85:334–338 (88).
Sosa et al. BBRC 161:305–311 (89).
Kalyanaraman et al., Aid Res and Hum. Retro. 4:319–329 (88).
90281606—abstract only Virology 177 (380-3) 1990.

*Primary Examiner*—Douglas W. Robinson
*Assistant Examiner*—S. Saucier
*Attorney, Agent, or Firm*—William M. Blackstone; Donna Bobrowicz

[57] ABSTRACT

Human Immunodeficiency Virus (HIV) glycoprotein gp160 is produced in its native form using a clone of HUT78 cells chronically infected with HTLV-III$_{451}$, known as 6D5$_{451}$, and grown in serum-free medium. gp160 is also produced in its native form using a clone of 6D5$_{451}$ that contains no HTLV-III virus.

3 Claims, 11 Drawing Sheets

① Glycoproteins eluted from Lentil-lectin Sepharose
② HTLV-III$_{451}$ gp160 from anti HIV-I gp41 Sepharose
③ Standard proteins

BIOSYNTHESIS AND SECRETION OF HIV-1 gp120 AND gp160 IN THE NON-PRODUCER CLONE-3 OF 6D5/451 CELLS

① 30 min. pulse labeling with $^{35}$S—methionine

②–⑥ : Chase of the label for 30 min., 1 hr, 2 hrs, 3 hrs, 4 hrs and 6 hrs.

7.5% PAGE

FIG.7

FIG.8A
UNCLONED 6D5/451

FIG.8B
CLONE 2

FIG.8C
CLONE 2

FIG.8D
CLONE 4

FIG.9c CEM50+CLONE 2

FIG.9b CEM50+6D5451

FIG.9e CEM50+CLONE 4

FIG.9a CEM50

FIG.9d CEM50+CLONE 3

PRESENCE OF HIV-1 SPECIFIC SEQUENCES IN THE CELL CLONES OF 6D5/451

The cellular DNA was digested with sac I enzyme and hybridized with full strength HTLV-III$_B$ specific probe.

① HTLV-III$_{451}$ in NHT cells ② Uncloned 6D5/451 cells.
③ CLONE-2 ④ CLONE-3 ⑤ CLONE-4

FIG.10

HIGH AFFINITY BINDING OF HTLV-111451 gp120 AND
gp160 SECRETED BY CLONED 6D5/451 CELLS

1

HUT-78 CELL LINES INFECTED WITH HTLV-III WHICH SECRETE GP160

The invention described herein was made during the course of work performed under National Cancer Institute, Department of Health and Human Services Contract No. NOI-CP-67694.

This application is a continuation-in-part of U.S. Ser. No. 07/362,548, filed Jun. 7, 1989, which is a continuation of U.S. Ser. No. 07/232,859, filed Aug. 16, 1988, now abandoned, all of which are incorporated herein by reference.

BACKGROUND OF THE INVENTION

The present invention relates to the production of native gp160 of human immunodeficiency virus (HIV), the etiologic agent of Acquired Immune Deficiency Syndrome (AIDS).

Human Immunodeficiency Virus (HIV) is now well established as the etiological agent of acquired immunodeficiency syndrome (AIDS). The virus is tropic for cells bearing the CD4 antigen and is highly cytopathic for helper-inducer (T4) cells. The envelope gene product of HIV is synthesized as a gp160 precursor molecule, which is subsequently processed into the external envelope protein gp120 and the transmembrane protein gp41. The precursor/product relationship between gp160 and the smaller proteins, gp120 and gp41, has now been well documented, as well as the amino acid sequences of all three [Allan et al, *Science*, 228:1091–1094 (1985) and Veronese et al, *Science*, 229:1402–1405 (1985)]. The external glycoprotein gp120 binds to the CD4 molecule on susceptible cells in the initial phase of viral cell fusion and giant cell formation induced by the virus [Dalgleish et al., *Nature*, 312:763–766].

In addition to their role in cell surface receptor recognition and cell fusion, HIV gp120 and gp41 are the primary targets for immune recognition in individuals infected with HIV. Hence, these proteins have received special attention in virus neutralization studies and vaccine development. It has been observed that large segments of gp120 expressed by recombinant DNA techniques, or native gp120 purified from HIV-infected cells, elicit mostly type-specific neutralizing antibodies in animals. In addition, the HIV envelope precursor protein gp160 expressed in insect cells with baculovirus vectors produced a strong type-specific immune response in goats [Rusche et al., *PNAS, USA* 84:6924–6928 (1987)].

The ability to infect certain cell lines with HIV, and to establish the infected cells into a continuous producer of intact virus has been described in U.S. Pat. No. 4,652,599. Even the ability to infect the cell line and the HIV variant of the present invention have been previously described [Getchell et al., *J. Clin. Microbiol.* 23:737–742 (1986)].

However, neither of these events alone permitted the establishment of a process capable of producing the HIV glycoprotein gp160 in its native form. Normally, native gp160 breaks down into gp120 and gp41. Consequently, the envelope protein obtained from cell culture media or from lysed virus is gp120 and gp41. It is therefore most surprising that gp160 may be obtained in its native form.

Glycoprotein gp160 has only been produced through recombinant means. However, recombinant gp160 is different than the native gp160, particularly in regard to glycosylation. These differences become critical in the search for an HIV vaccine, particularly since the envelope glycoproteins of HIV determine viral tropism and harbor epitopes which are essential for the development of neutralizing antibodies against the virus.

SUMMARY OF THE INVENTION

It is an object of the present invention to provide a unique clone of HUT78 cells which, when chronically infected with HTLV-III$_{451}$, releases functionally intact viral glycoprotein gp160 into the extracellular medium.

Another object of the present invention is to provide an immortalized cell line grown in a serum-free medium under such conditions that the cell line releases gp160 in its native form into the medium.

Yet another object of the present invention is to provide intact HIV gp160 in its native form.

These and other objects and advantages of the invention are accomplished by growing infected cell line 6D5$_{451}$ in a serum-free medium, and isolating the native gp160 released by the cells into the medium.

Another object of the present invention is to provide a unique clone of HUT78 cells which are free from HIV-1 virus and viral particles, but which release intact HIV gp160 in its native form into the extracellular media.

Another objective is to provide an immortalized cell line of the HIV-1 free clone which releases native gp160 into the medium.

DESCRIPTION OF THE FIGURES

FIG. 3 shows the inhibition of HIV-induced syncytium formation by HTLV-III$_{451}$ glycoproteins. CEM cells were cocultivated with Molt-3/HTLV-III$_B$ cells as described below. The cells were photographed after 48 hours. To study the effects of the viral glycoproteins, CEM cells were pre-incubated for 1 hour with the proteins before cocultivation.

FIG. 4 shows the binding of gp120 and gp160 by CD4. Conditioned medium from a $^{35}$S-methionine labeled 6D5$_{451}$ culture was clarified by centrifugation at 2000×g followed by filtration through a 0.45 u filter. One-half milliliter of the medium was incubated with CEM$_{50}$ cells in a total volume of 2 m., as described below. The bound proteins were immunoprecipitated with OKT4 antibody. Lane 1: 0.5×10$^6$ cells; Lane 2: 1×10$^6$ cells; Lane 3: 2×10$^6$ cells; Lane 4: 5×10$^6$ cells; Lane 5: 10×10$^6$ cells; Lane 6: 20×10$^6$ cells.

FIG. 8 is a group of electron micrographs of both uncloned and cloned cells containing viral material.

FIG. 9 shows the ability of the cloned and uncloned cells to fuse with CD4 positive CEM$_{50}$ cells.

DESCRIPTION OF PREFERRED EMBODIMENTS

We have discovered a method to produce native human immunodeficiency virus gp160 by the following steps:

infecting cells from a HUT78 T-cell line with HTLV-III$_{451}$, selecting the infected cells that produce native gp160, cloning the selected cell line, selecting at least one clone from the selected cell line that produces native gp160, but which does not produce HTLV-III virus, propagating the non-HTLV-III producing cloned cell, incubating the cloned cell line under conditions that promote the production of gp160 and isolating native gp160 from the surrounding medium or from the cells.

A single cell clone of HUT78 cells has been infected with Human Immunodeficiency Virus Type 1 (HIV-1), whereby the infected cell line has become a continuous producer of virus.

Clone 6D5 is susceptible to chronic infection with HIV-1, as described in Getchell et al., *J. Clin. Microbiol.*, 23:737–742 (1986). Clone 6D5 was infected with a specific strain of HIV-1, HTLV-III$_{451}$, and produced the infected cell line 6D5$_{451}$. The infected cell line was then grown in serum-free medium, by pelleting 6D5$_{451}$ cells and then resuspending the cells in serum-free medium (such as HB101 medium, commercially available from E. I. du Pont de Nemours & Co. Inc.). Serum-free medium HB104, also available from Du Pont, may also be used in the practice of this invention.

Only when serum-free medium is used can glycoprotein gp160 be separated from other proteins in the media. gp160 cannot be excluded from other media components when serum-containing media is used.

In the preferred embodiment, the HB101 medium also contains growth supplements such as transferrin, insulin, and bovine serum albumin. To assist in the growth of cells, the cells were subcultured every four days. The 6D5$_{451}$ cells were grown for 2 to 3 generations. The amount of HIV proteins released into the media, as measured by extracellular reverse transcriptase activity, was nearly five-fold greater in serum-free medium than in serum-containing medium. Reverse transcriptase ("RT") in the culture medium of the infected cells was analyzed with (dT)~15-(A)$_n$ as primer template, as described in Poiesz et al., *PNAS, USA*, 77:7415–7419 (1980).

Figure 1:
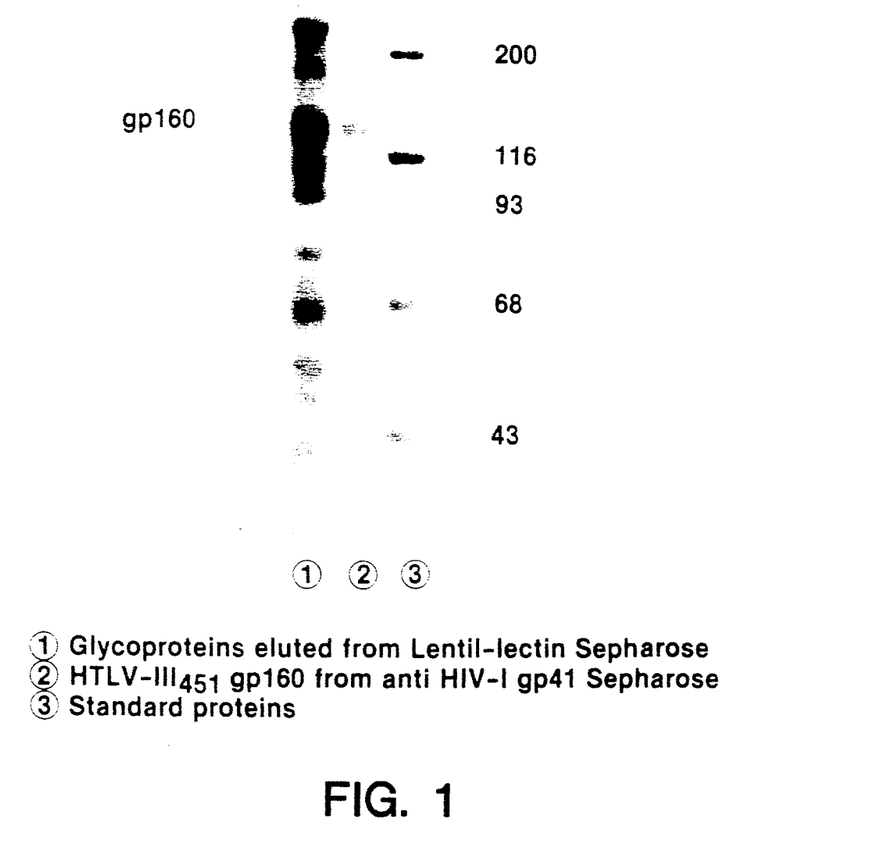
FIG. 1 (lane 1) shows the SDS-PAGE profile of the glycoprotein eluted from the lentil lectin Sepharose ®. Lane 2 shows the purified gp160 stained with Coomassie blue.

The cell-free medium was used as the source of the glycoprotein. The medium was adjusted to 20 mM sodium phosphate, pH 7.5, 0.5% Triton X-100 ® (Rohm & Haas Company, Philadelphia, Pa), 0.1 mM phenylmethylsulfonyl fluoride, and 400 mM sodium chloride. After incubation at room temperature for one hour, the medium was concentrated 30-fold with a Pellicon cassette system, commercially available from Millipore Corp. Extraneous proteins derived from the media supplement were removed from the concentrate by immunoaffinity absorption (overnight) with a Sepharose ®-bound goat antibody (Pharmacia LKB Biotechnology, Inc.) raised against the proteins in the growth supplement in the serum-free medium. Proteins which bound to the goat antibody were removed, and the unbound material was then passed through a lectin affinity column, preferably a lectin-Sepharose ® column. Although the use of a lentil lectin column is preferred, other lectins which will recognize mannose, such as concanavalin-A, may also be employed. After washing with phosphate buffered saline (PBS), the column was eluted with 400 mM alpha-methylmannoside in order to recover the viral glycoprotein. Although the use of methylmannoside to elute the column is preferred, any mannose, pyranoside, or saccharide which competes with the lectin in the affinity column may be used. FIG. 1 (lane 1) shows the SDS-PAGE profile of the glycoprotein eluted from the lentil lectin-Sepharose ®. The prominent glycoproteins in the samples were the 120 and 160 kD proteins. These proteins also reacted strongly in immunoblots with HIV-1 antibody-positive human serum. The immunoblot analysis of HTLV-III$_{451}$ glycoprotein is carried out by a well known procedure, such as described in Sarngadharan et al., *Science* 224:506–508 (1984). Essentially, the proteins are run on 7% SDS-polyacrylamide gels and transferred to nitrocellulose strips. The nitrocellulose strips are then treated with the appropriate antibodies, and the blots are developed with peroxidase-conjugated secondary antibodies; the bands are visualized by reacting the strips with diaminobenzidine.

gp160 was purified from the mixture of glycoproteins eluted from lentil-lectin Sepharose ® column by immunoaffinity chromatography using a monoclonal antibody to HIV-1 gp41 protein. The monoclonal antibody was developed using partially purified HTLV-III$_{451}$ glycoproteins by standard techniques. The immunoglobulin fraction of the antibody was coupled to Sepharose ® according to the method described by the manufacturer, Pharmacia LKB Biotechnology, Inc. The eluate from the lentil-lectin Sepharose ® column was equilibrated at 4° C. with the anti-HIV-1 gp41 Sepharose ® in 20 mM Tris-HCl, pH 8.5 containing 0.5% Triton X-100 ®, 1 M potassium chloride, and 0.1 mM phenylmethyl sulfonyl fluoride (PMSF). The Sepharose ® was then packed in a column, washed with PBS and the bound protein was eluted with 100 mM sodium bicarbonate. The HTLV-III$_{451}$ gp160 eluted from the column in a nearly homogenous state. FIG. 1 (lane 2) shows the purified gp160, separated by SDS-PAGE and stained with Coomassie blue.

Figure 5:
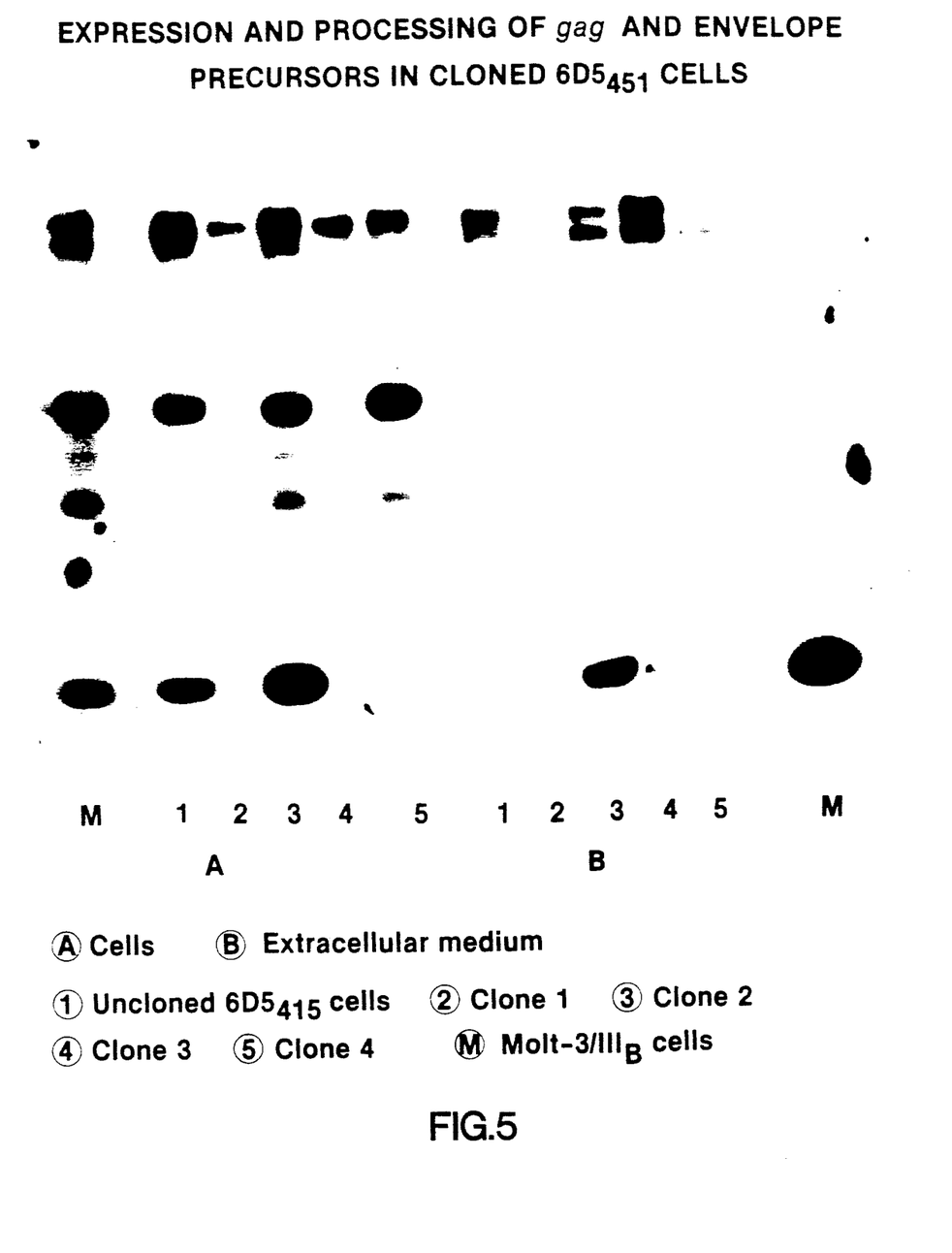
FIG. 5 shows the radioimmunoprecipitation of HIV-1 proteins synthesized by 6D5$_{451}$ cell clones.

Four clones of the 6D5$_{451}$ cells were isolated by limiting dilution for further analysis. The cells were labeled with $^{35}$S-Methionine for seven hours, after which time the labeled cellular proteins were analyzed by immunoprecipitation with an HIV-1 antibody positive human serum. As seen in FIG. 5, lane 4, clone 3 synthesized only gp120 and gp160 and did not synthesize the gag precursor p55. In lane 3, clone 2 showed the normal pattern of viral protein synthesis. Clone 4, as seen in lane 5, had only the envelope proteins and synthesized, but did not process, the gag precursor protein p55. The labelled viral proteins in the medium reflected the intracellular profile of the viral proteins. All clones secreted both gp120 and gp160 in the medium while only the uncloned cells and clone 2 had p24, as seen in lanes 5–8. The labeled medium was centrifuged at 100,000 g for one hour to separate the particulate material and similar radioimmunoprecipitation. Analysis showed that most of the gp120 and gp160 in the cloned and uncloned cells was not associated with the virus pellet.

Since there was a slight difference in the mobilities of the intracellular and extracellular gp160 in the uncloned $6D5_{451}$ cells, the labeled proteins were analyzed at a lower percentage of the acrylamide gel after immunoprecipitation with monospecific antibodies to gp120 and gp41 of HIV-1. This analysis revealed the existence of two intracellular forms of gp160 in clones 2 and 4 and only the lower molecular weight form in clone 3. Only the lower molecular weight form of gp160 was secreted in the extracellular medium.

The relationship between the two forms of gp160 and gp120 was further analyzed by pulse labelling uncloned and clone 3 cells for 30 minutes and chasing the label in unlabeled complete medium. Both gp120 and the lower molecular weight form of gp160 were secreted in the medium simultaneously from the beginning of the two hour chase period and continued to accumulate during the course of the experiment. No higher molecular weight form of gp160 was found in the medium.

The RT activity in the medium was also examined. For this purpose the cells were resuspended in fresh medium at a density of $0.25 \times 10^6$ cells per ml and the RT activity in the medium was determined. All clones exhibited similar cell growth. Clones 3 and 4 did not have any RT activity in the medium. Clone 2, as expected, had high levels of RT which was about six times that of with uncloned $6D5_{451}$ cells.

Electron microscopy of the various cells demonstrated that the uncloned $6D5_{451}$ cells contained primarily immature viral capsids and a few mature virus particles while clone 2 had mostly mature virus, including those with a central dense rod like core, as seen in FIG. 8. The presence of a few immature virus structures is indicative of the altered processing of the envelope proteins in these cells. Clone 4 exhibited immature viral capsids with the presence of an occasional mature virus. Clone 3 lacked all virus and any intracellular or extracellular capsid structures.

In view of the modified processing of the envelope proteins and the incomplete assembly of the virus in the cloned $6D5_{451}$ cells, we examined the ability of these cells to fuse with CD4 positive cells, a typical property of the HIV-1 infected cell lines. The cloned cells were mixed with highly CD4 positive $CEM_{50}$ cells and the cultures were analyzed 24 to 48 hours later. Only the uncloned, clone 2 and clone 4 cells formed syncytia with the CEM cells, while clone 3, which also expressed high levels of both gp120 and gp160, did not form any syncytia.

The differences in the expression of the viral proteins in $6D5_{451}$ cells described above may either be due to large deletions in the HIV-1 genome or due to minor changes in the integrated provirus which led to the differential regulation of viral gene expression. To examine the nature of the integrated provirus, high molecular weight DNA from these cells was digested with SacI restriction enzyme, separated in agarose gel and hybridized with the labeled probe from the complete genome of HIV-1 probe. All clones contained the expected hybridizable fragments of 5.5 and 3.5 Kb. The clones also contained a 4.5 Kb fragment which was not present in $HTLV-III_{451}$ infected primary human T-cells.

Identification of cell clones from the chronically infected cell line $6D5_{451}$ has enabled us to characterize nonproducer cell lines with differing ability to process and secrete viral proteins. Two different forms of intracellular gp160 were synthesized in these cells. Clones 2, 3 and 4 made the lower molecular weight form of gp160 while the higher molecular weight form of gp160 was seen only in clones 2 and 4. Both forms of gp160 were processed to gp120 but only the lower molecular weight form was secreted in the medium in addition to gp120.

Figure 11:
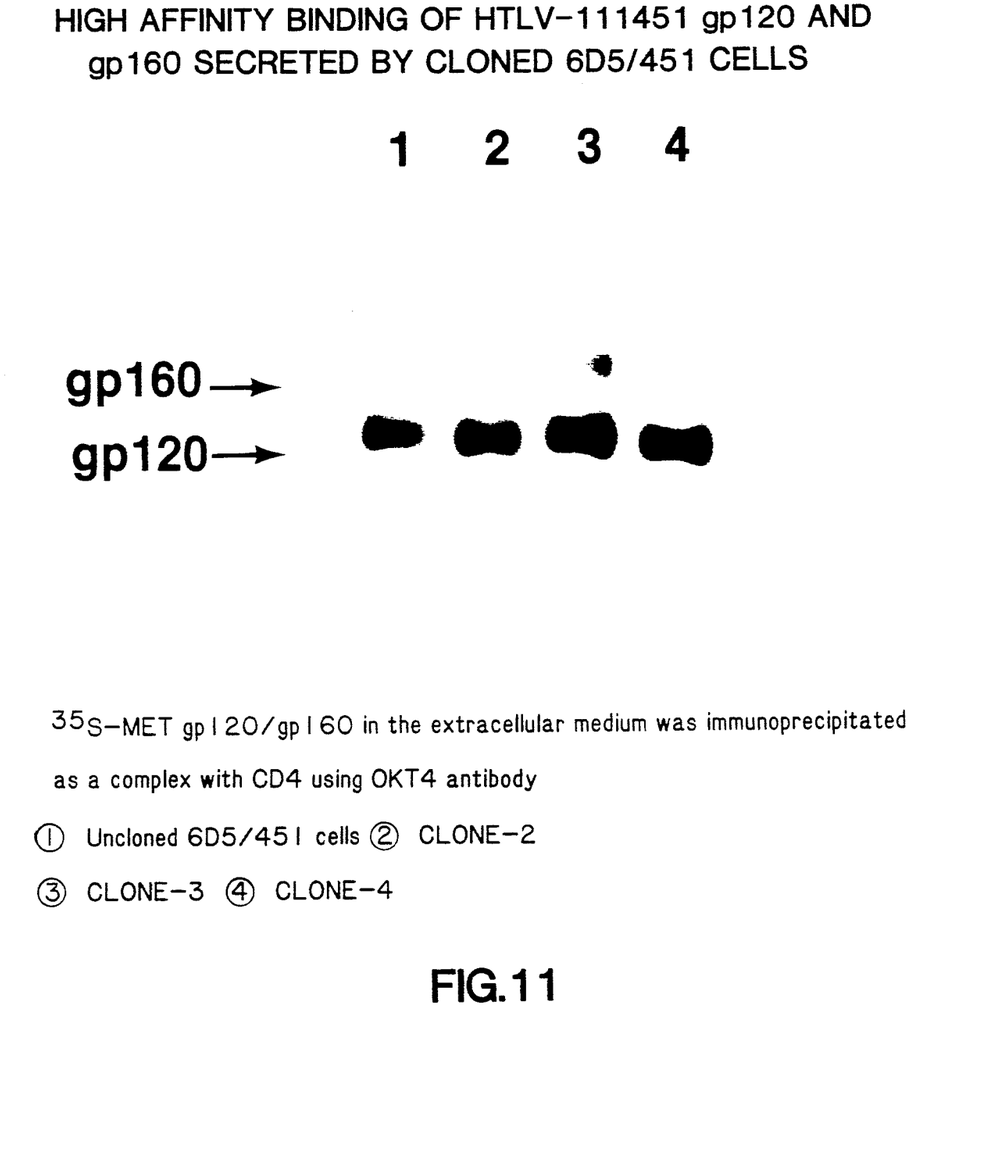
FIG. 11 shows the formation of CD4-gp120/gp160 complexes by secreted envelope proteins of 6D5$_{451}$ cell clones.

The pronounced differences in the processing of the viral proteins in the cell clones of the $6D5_{451}$ cell line also resulted in the biological heterogeneity in the cells. Only clone 3 produced gp160 while containing no HIV-1 particles. While clone 2, which expressed the full complement of the viral proteins released mostly mature virus particles, clone 4 which was defective in gag proteins and RT had immature viral capsids. Clone 3 did not form syncytia with CD4 positive cell line $CEM_{50}$, while clones 2 and 4 formed good syncytia. This may be due to the synthesis and processing of only the lower molecular weight form of gp160 in clone 3. All the expressed gp120 and gp160 from all the $6D5_{451}$ clones formed high affinity complexes with CD4, as shown in FIG. 11. This is further substantiated by our previous observation that the secreted gp160 from the uncloned cells is properly processed in the uncloned $6D5_{451}$ cells and binds with comparable affinity to cellular CD4 (Kalyanaraman et al., AIDS Research and Human Retrovirus, in press, to be published 1990.) Hence it is possible that the lack of gag gene expression contributed significantly to the biological difference in clone 3.

Glycoprotein gp160 and its derivatives, prepared according to the present invention, may be employed in a conventional manner in immunotherapeutic and/or immunodiagnostic methods and compositions. Such methods of treatment and quantities employed are well-recognized in the art, and may be chosen by those of skill in the art from available methods and techniques. For example, gp160, as produced in accordance with the present invention, may be combined with a pharmaceutically acceptable adjuvant in an amount effective to provide diagnostic utility in an ELISA assay.

In particular, gp160 may now be prepared according to the present invention, in cells free of HIV-1 virus or particles, thereby making the laboratory safe from accidental contamination by the virus.

Although the above description of the invention includes a recitation of preferred embodiments, this is not intended to limit the invention.

In order that the invention herein described may be more fully understood, the following Examples are set forth. It should be understood that these examples are for illustrative purposes only, and are not to be construed as limiting the invention in any manner.

EXAMPLES

EXAMPLE 1

Twenty million 6D5$_{451}$ cells were labeled for 15 hours in 10 ml of the HB101 serum-free medium, containing 5% of the normal amount of methionine, 1 mCi of $^{35}$S-methionine, and 5% dialyzed HB101 supplement. The cell-free supernatant was filtered through a 0.45 micron filter, concentrated, and treated with 0.5% Triton X-100®, 500 mM sodium chloride, and 1 mM PMSF. After one hour at room temperature, the solubilized medium was mixed with an equal volume of PBS containing 0.5% Triton X-100®, 1% deoxycholate, and 0.1% sodium dodecyl sulfate (PBS-TDS). One milliliter of the mixture was incubated overnight with 10 ul of an anti-HIV serum and 150 ul of 10% protein-A Sepharose®. The Sepharose® was pelleted, washed four times with PBS-TDS and boiled for 2 minutes with 1% SDS, 1% beta-mercaptoethanol, and 125 mM Tris-HCl (pH 6.8). The solubilized labeled proteins were separated on 7.5% SDS polyacrylamide gel and autoradiographed as described in Veronese et al, *Science* 229:1402-1405 (1985).

Figure 2:
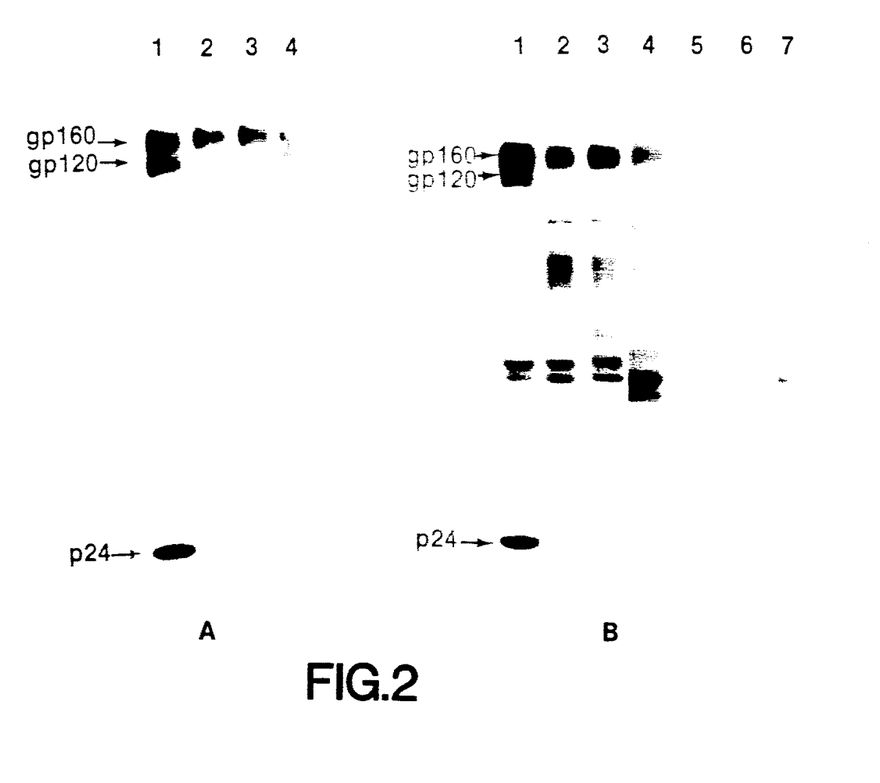
FIG. 2 shows the release of HIV-specific proteins by 6D5$_{451}$ cells. Panel A: medium from cells grown in FCS; Panel B: medium from cells grown in HB101. Lane 1: HIV-positive human serum; Lane 2: rabbit anti-HTLV-III$_B$ gp41; Lane 3: rabbit anti-121 peptide (Centocor); Lane 4: goat anti-HTLV-III$_B$ gp120; Lane 5: normal human serum; Lane 6: normal rabbit serum; Lane 7: normal goat serum.

FIG. 2 shows gp160 as a distinct immunoreactive protein product in the culture medium.

EXAMPLE 2

The viral proteins in the extracellular medium of 6D5$_{451}$ cells grown in serum-free medium were analyzed by metabolic labeling with $^{35}$S-methionine, as described above. The released radioactive proteins were immunoprecipitated with either HIV-1 seropositive human serum or antibodies specific to HTLV-III$_B$ gp120 or gp41. HIV-1 positive human serum precipitated, in addition to the major core protein (p24), two proteins of approximately 120 kD and 160 kD. A goat antibody to HTLV-III$_B$ gp120 precipitated both 120 kD and 160 kD proteins, suggesting that they contain immunoreactive domains of gp120. On the other hand, rabbit anti-gp41 immunoprecipitated only the 160 kD protein. These results indicate that the 160 kD protein has both gp120 and gp41 domains in HIV, while the 120 kD protein has only the gp120 epitopes of HIV.

EXAMPLE 3

The native 120 and 160 kD glycoproteins produced in accordance with this invention were further characterized by their reactivities with antibodies specific for HTLV-III$_B$ gp120 and gp41. For this purpose, the proteins were separated by SDS-PAGE, transferred to nitrocellulose strips, and treated with antibodies specific to HTLV-III$_B$ gp120 and gp41. Both the 120 and 160 kD proteins reacted with the HIV-1 positive serum, and with the goat anti-gp120. Only the gp160 kD protein reacted with the antibodies to HTLV-III$_B$ gp41. Of the two monoclonal antibodies to gp120 used, only one reacted with both, showing type-specific reactivities of the monoclonal antibodies with different isolates of HIV.

EXAMPLE 4

Figure 3A:
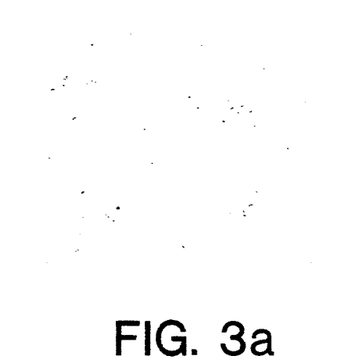
FIG. 3A: untreated CEM cells.
Figure 3B:
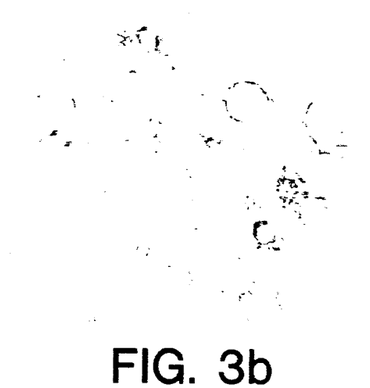
FIG. 3B: CEM cells plus Molt-3/HTLV-III$_B$ cells.
Figure 3C:
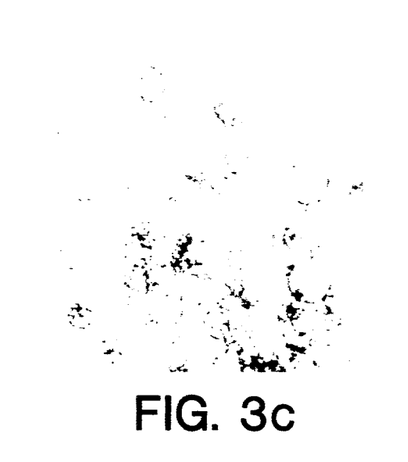
FIG. 3C: CEM cells pretreated with glycoproteins from uninfected 6D5 cell culture.
Figure 3D:
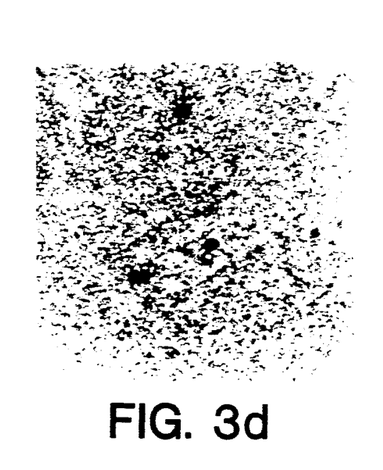
FIG. 3D: CEM cells pretreated with 6D5$_{451}$ glycoproteins.
Figure 4:
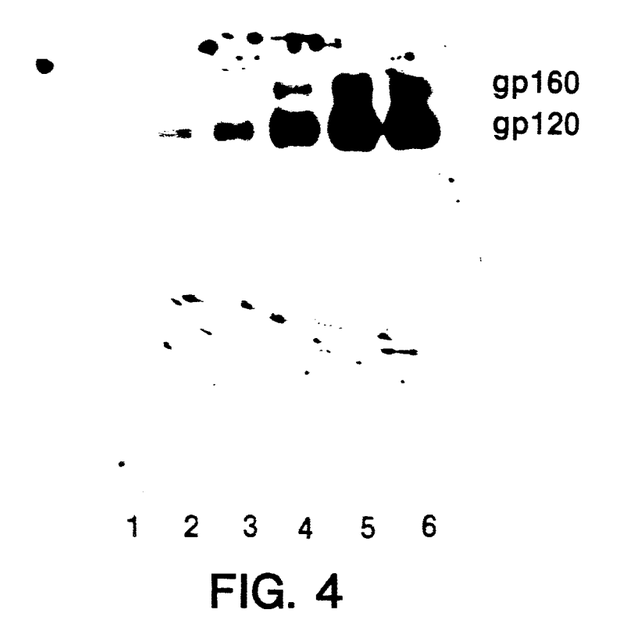

Although the primary target of HIV-1 infection is the helper/inducer subset of T lymphocytes bearing CD4 cell surface markers, the actual mechanism by which the virus infects susceptible target cells is only beginning to be understood. Monoclonal antibodies to certain epitopes of CD4 antigens were found to block viral infection and could immunoprecipitate complexes of CD4 and gp120. This tends to suggest that the key interaction between the gp120 and CD4 initiates the infection process of HIV-1. One consequence of the virus infection is the formation of multinucleated giant cells resulting from cell fusion events. A clone of CEM cells has been shown to exhibit rapid and quantitative syncytia formation when mixed with HIV-1-infected cell lines [Mathews et al., *PNAS, USA* 84:5424-5428 (1987)] (FIG. 3B). This type of syncytia formation often serves as a measure of gp120-CD4 interaction during virus infection. The ability of HTLV-III$_{451}$ glycoprotein to interfere with HTLV-III$_B$-induced fusion of CEM cells was assayed by incubation of the target CEM cells with a partially purified preparation of glycoprotein before mixing with Molt-3/HTLV-III$_B$ cells for 36 hours. Preincubation of CEM cells with glycoprotein preparations from uninfected 6D5 cells had no effect on the syncytia formation (FIG. 3C). In contrast, pretreatment of the CEM cells with the HTLV-III$_{451}$ glycoprotein preparations completely blocked the synctia formation induced by HTLV-III B/Molt-3 cells (FIG. 3D). This suggests that the viral glycoprotein could selectively bind with CD4 antigens on target cells, thereby blocking infection by the HIV-1 infected cells.

By immunoprecipitation with a human serum, more than 90% of the viral glycoproteins were found in the soluble form after high speed centrifugation of the conditioned medium. The interaction of HTLV-III$_{451}$ glycoprotein with the CD4 molecule was further examined by the specific binding of labeled gp120 and gp160 to CEM cells. For this purpose, cell-free supernatant from $^{35}$S-methionine labeled 6D5$_{451}$ was incubated with increasing numbers of CEM cells. After washing the cells with PBS, the bound HIV glycoprotein-CD4 complex on the cells was solubilized with detergents as described above. The solubilized extract was immunoprecipitated with two monoclonal antibodies to the CD4 molecule. Both HIV glycoproteins were precipitated by OKT4. When the receptor density was limiting, gp120 was the predominant species that was bound to the cells. At higher cell density, when binding sites were more abundant, both gp160 and gp120 were clearly evident in the CD4 complex. The CD4-glycoprotein complex could not be precipitated with the monoclonal OKT4A. This is consistent with the previous observations that the site of attachment of HIV gp120 on the CD4 molecule is the OKT4A epitope. The relative affinity of the receptor site appears to favor gp120 over gp160 based on the observation that virtually no gp160 was bound from a mixture of gp120 and gp160 at limiting CD4 concentrations. How much of this difficulty of binding is dictated by topological constraints on the larger gp160 in approaching the cell surface CD4 is yet to be determined.

EXAMPLE 5

Cloning 6D5 451 Cells

The 6D5$_{451}$ cell clones were obtained by seeding the uncloned cells from Example 1 in a 96 well microtiter plate such that only one in three wells contained one cell. The clones 1, 2, 3, and 4 were developed from a single cluster of cells and were expanded and investigated further. Clone 3 was deposited at the American Type Culture Collection (ATCC), 12301 Parklawn Drive, Rockville, Md., 20852, USA, and given ATCC #designation CRL 10307.

EXAMPLE 6

Metabolic Labeling and Radioimmunoprecipitation Analysis of 6D5451 and Clone 3

Cells ($1 \times 10^6$ per ml) chronically infected with HIV-1 were labeled for seven hours in methionine free RPMI 1640 medium containing 2% dialyzed fetal calf serum and 100 uC per ml of $^{35}$S Methionine. The cells were pelleted by centrifugation for 10 minutes at 1000 g and the labeled medium was filtered through a 0.45 u Millipore filter. The cells and the medium were solubilized in PBS containing 1% Triton X-100 ®, 0.5% deoxycholate, 0.1 percent SDS and 0.1 mM PMSF (PBS-TDS). The cells were freeze-thawed twice and centrifuged at 100,000 g for 30 minutes and the supernatant was used for further analysis. One milliliter of PBS-TDS containing 0.5 mL of solubilized cells or medium was preabsorbed for three hours with 10ul of normal human serum and 200 ul of 10% Protein-A Sepharose ® at room temperature. The mixture was centrifuged at 3000 g for ten minutes and 1 ml of the supernatant was incubated with 10 ul of HIV-1 positive human serum and 150 ul of Protein-A Sepharose ® overnight at 4° C. The mixture was centrifuged and the pellet was washed three times with PBS-TDS. The pellet was boiled with 1% SDS and 1% 2-mercaptoethanol for two minutes and centrifuged at 3000 g for 10 minutes. The supernatant was separated in polyacrylamide gel and the labeled proteins were visualized by fluorography.

For pulse chase analysis of freshly labeled proteins the cells were labeled with $^{35}$S methionine as above for 30 minutes, and resuspended in complete medium without labeled methionine. The labeled proteins were analyzed at specified time intervals.

Figure 6:
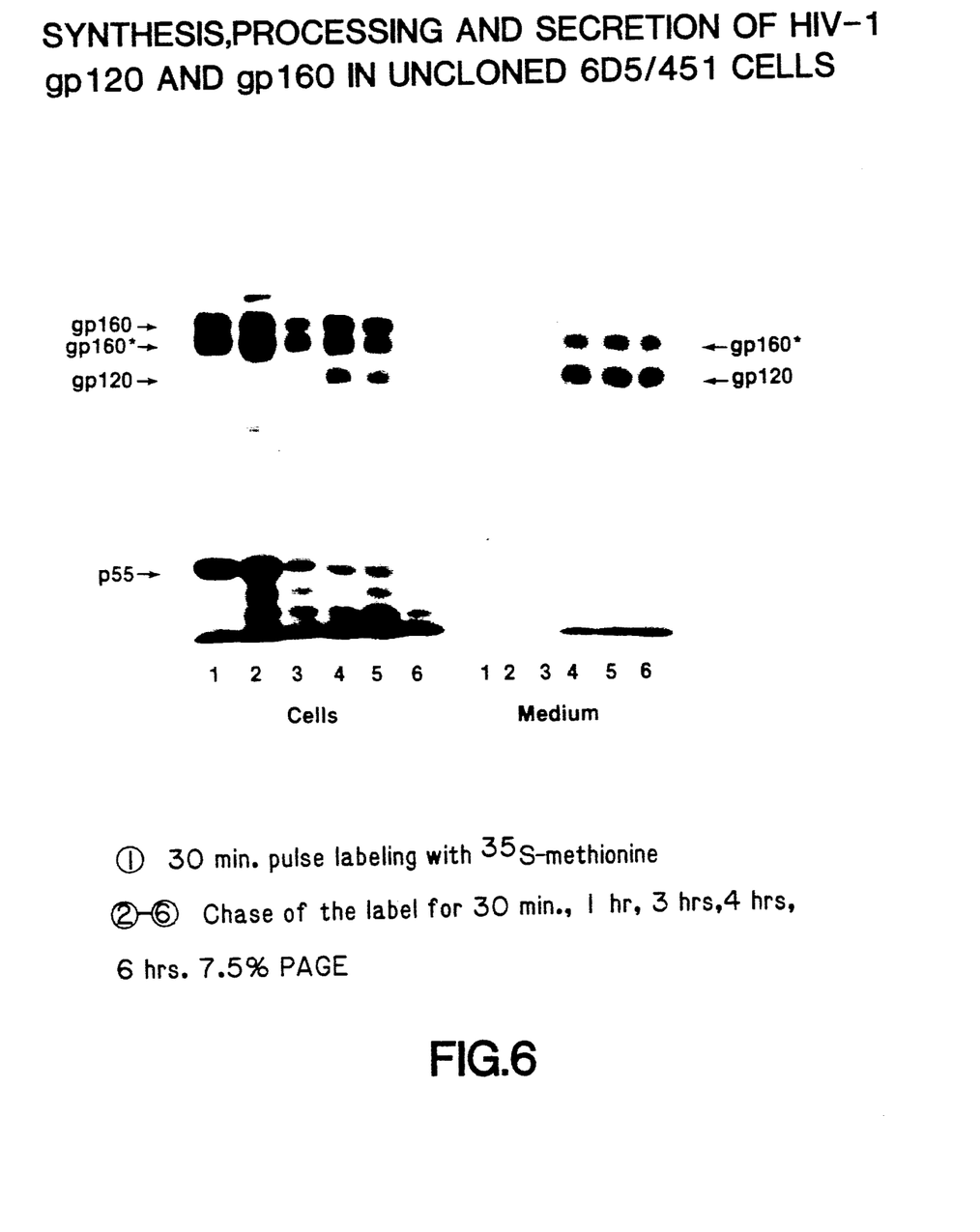
FIG. 6 shows the pulse chase analysis of HIV-1 proteins synthesized by uncloned 6D5$_{41}$ cells.
Figure 7:
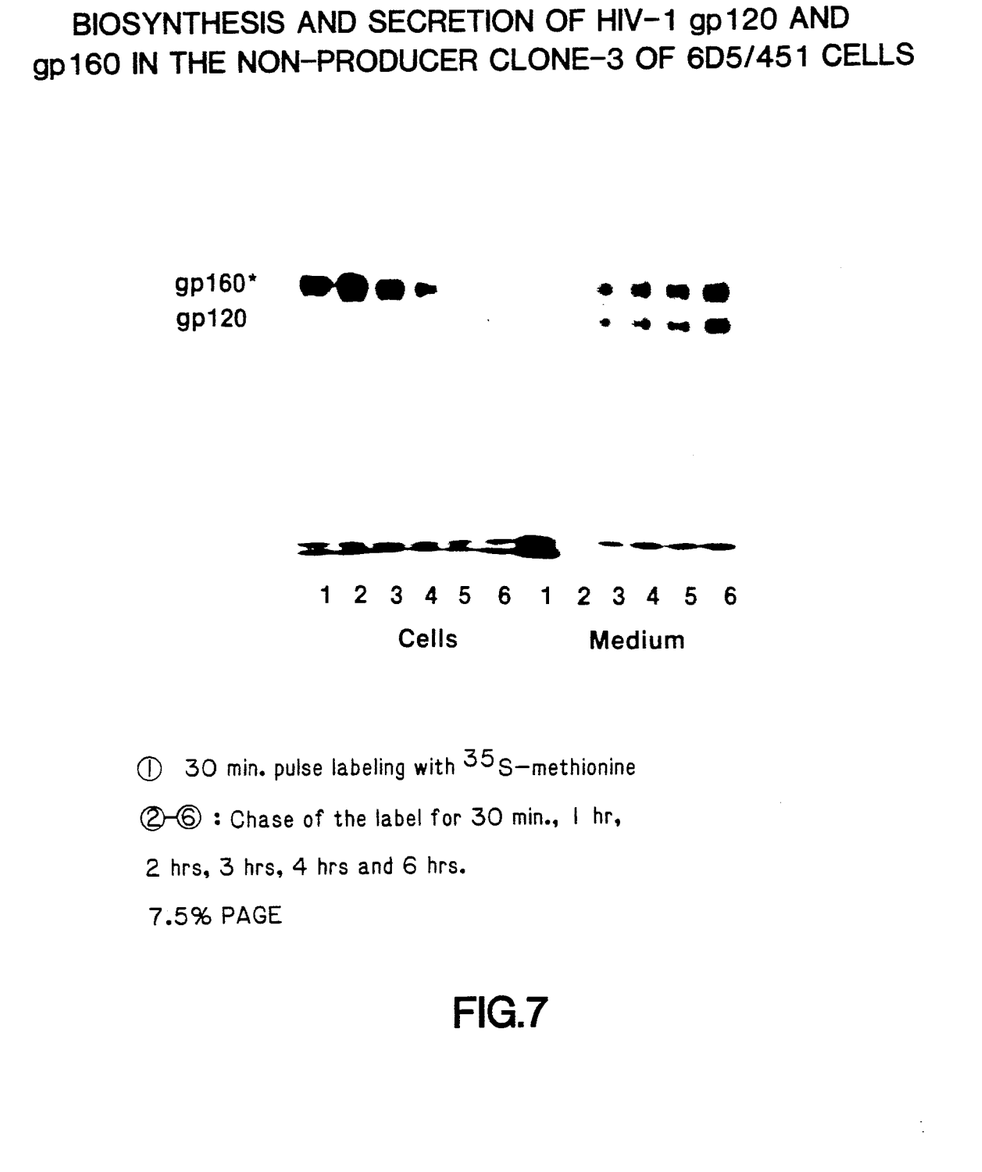
FIG. 7 shows the synthesis of HIV-1 proteins in 6D5$_{451}$ clone 3 cells.
Figure 8A:
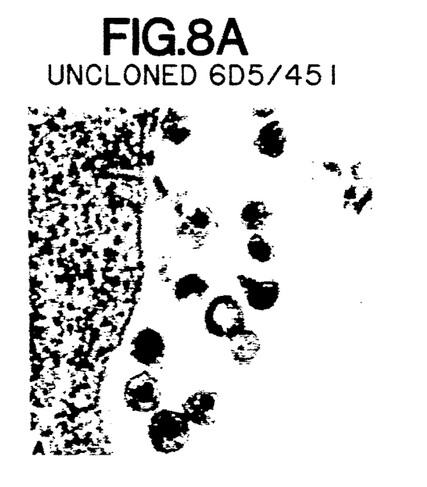
FIG. 8A shown uncloned 6D5$_{451}$.
Figure 8B:
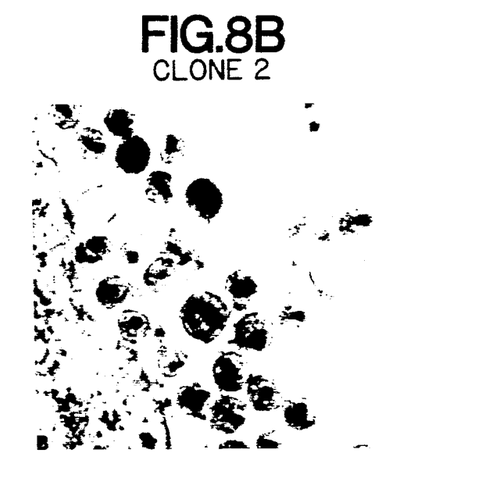
FIG. 8B and FIG. 8C shown Clone 2.
Figure 8C:
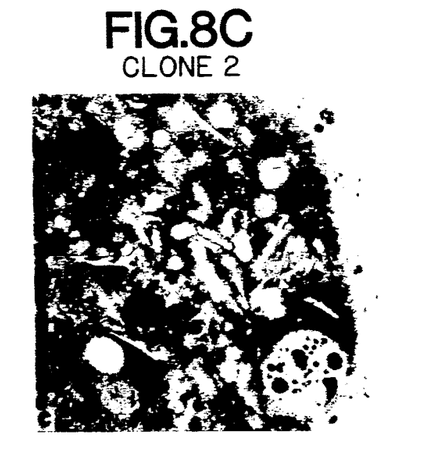
Figure 8D:
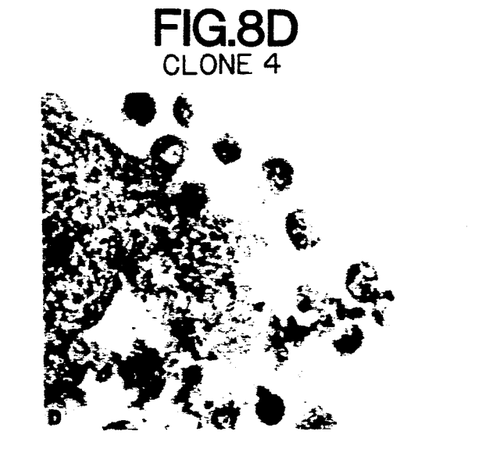
FIG. 8D shows Clone 4.
Figures 9A, 9B:
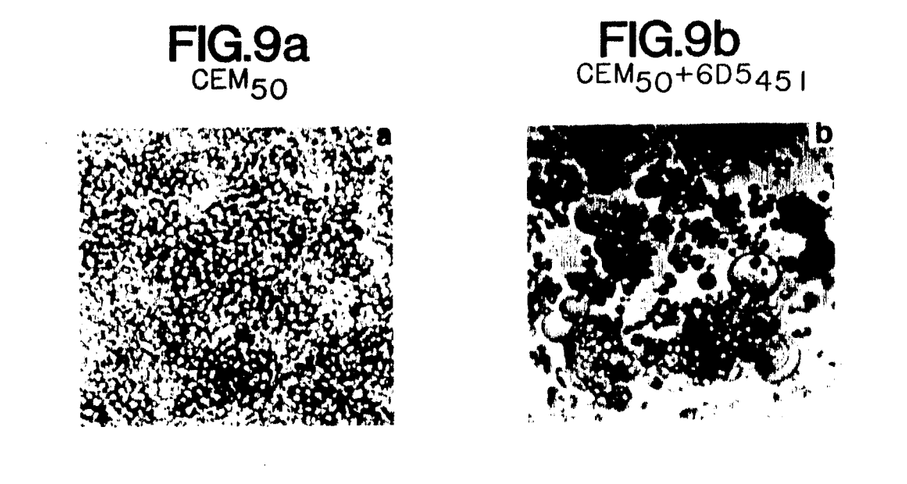
FIG. 9A shows CEM$_{50}$ cells alone.
FIG. 9B shown CEM$_{50}$ cells with 6D5$_{451}$.
Figure 9C:
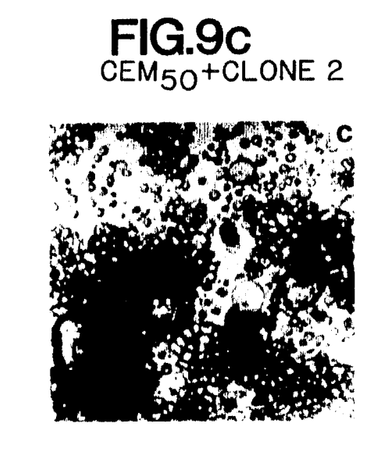
FIGS. 9C, 9D and 9E shown CEM$_{50}$ cells with Clones 2, 3 and 4, respectively.
Figure 9D:
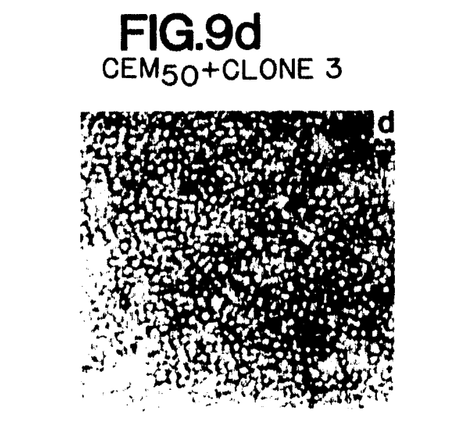
Figure 9E:
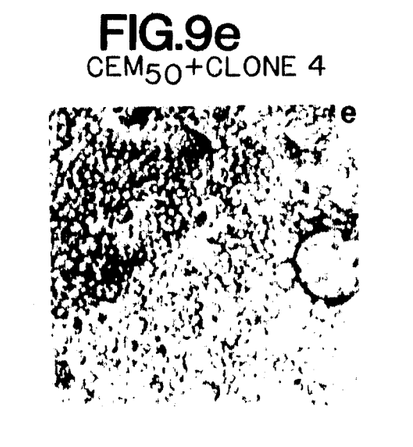

As seen in FIG. 6 for the uncloned 6D5451 cells and in FIG. 7 for clone 3 cells, both forms of gp160 were synthesized during the pulse (lane 1), and gp120 was seen only after two hours of chase of the label in the uncloned cells. During the subsequent chase period the label began to disappear from both forms of gp160. The lower molecular weight form of gp160 and gp120 were secreted simultaneously in the medium from the start of the two hour chase period and continued to accumulate during the course of the experiment. No higher molecular weight gp160 was found.

EXAMPLE 7

Syncytia Formation Assay $1 \times 10^5$ highly CD4 positive cells, the CEM$_{50}$ clone of the CEM cell line, obtained from Dr. T. Mathews of Duke University, N.C., were mixed with $1 \times 10^4$ HIV-1 infected cells in a total volume of 200 ul in a 96 well microtiter plate, were incubated for 24 to 36 hours and were photographed.

As shown in FIG. 9, clone 3 cells did not form syncytia with the CEM cells, whereas the uncloned cells, clone 2 and clone 4 cells formed syncytia with these CEM cells.

EXAMPLE 8

Analysis of CD4-gp120 or gp160 Complexes 200 ul of the extracellular medium from metabolically labeled uncloned 6D5451 cells and clone 2, 3, and 4 cells were incubated with $5 \times 10^6$ CEM$_{50}$ cells for two hours at room temperature in a total volume of 1 ml of the binding medium (RPMI 1640 medium containing 2 mg/ml of bovine serum albumin (BSA) and 0.1 mM PMSF). The cells were then pelleted, washed three times with PBS and solubilized in 1 ml of PBS-TD buffer (PBS containing 1% Triton X-100 ®, 0.5% deoxycholic acid and 0.1 mM PMSF). The sample was centrifuged at 10,000 rpm in a microfuge and the supernatant was incubated overnight at 4° C. with 20 ul OKT4 antibody and 200 ul of Protein-A Sepharose ® (equilibrated with rabbit anti-mouse IgG, K chain). The Sepharose ® was pelleted and washed three times with PBS-TD buffer and boiled with buffer containing 1% SDS and 1%-mercaptoethanol. The eluted labeled proteins were separated in 7.5% polyacrylamide gel and visualized by fluorography.

As seen in FIG. 11, all the expressed gp120 and gp160 from all cloned cells formed high affinity complexes with CD4.

EXAMPLE 9

Reverse Transcriptase Assay

Uncloned 6D5451 cells and clone 2, 3, and 4 cells were examined for reverse transcriptase activity in the media. The cells were resuspended at a density of $0.25 \times 10^6$ cells/mL of fresh medium as described above. The assay was carried out as described in Poiesz et al., 77 Proc. Nat. Acad. Sciences 7415-7419 (1981). 2 ml of culture medium was treated with 1 ml of 30% polyethylene glycol for two hours at 4° C. and the virus was pelleted by centrifugation at 300 RPM for 10 minutes in a Beckman centrifuge. The virus was solubilized and the RT was assayed using rAdT as template primer. All clones exhibited similar cell growth.

TABLE 1

| PROPERTIES OF CLONED 6D5451 CELLS | | | | |
|---|---|---|---|---|
| Property | Uncloned | Clone 2 | Clone 3 | Clone 4 |
| Expression of gp120 and gp160 | + | + | + | + |
| Expression of gag proteins | p24, p55 | p24, p55 | — | p55 |
| Extracellular RT | + | + | — | — |
| Induction of syncytia in CEM 50 | + | + | — | + |
| Particles by EM | + | + | — | — |

As seen in Table 1, clones 3 and 4 did not have any RT activity in the medium. Clone 2 had high levels of RT which was approximately six times greater that that of the uncloned 6D5451 cells.

EXAMPLE 10

Southern Blot Analysis

High molecular weight DNA was extracted from uncloned 6D5451 cells, and from clone 2, 3, and 4 cells, was digested with Sac-1 restriction enzyme and the HIV-1 specific fragments were identified as described by Ratner et al., 1984, using HTLV-III$_B$ specific probe.

Figure 10:
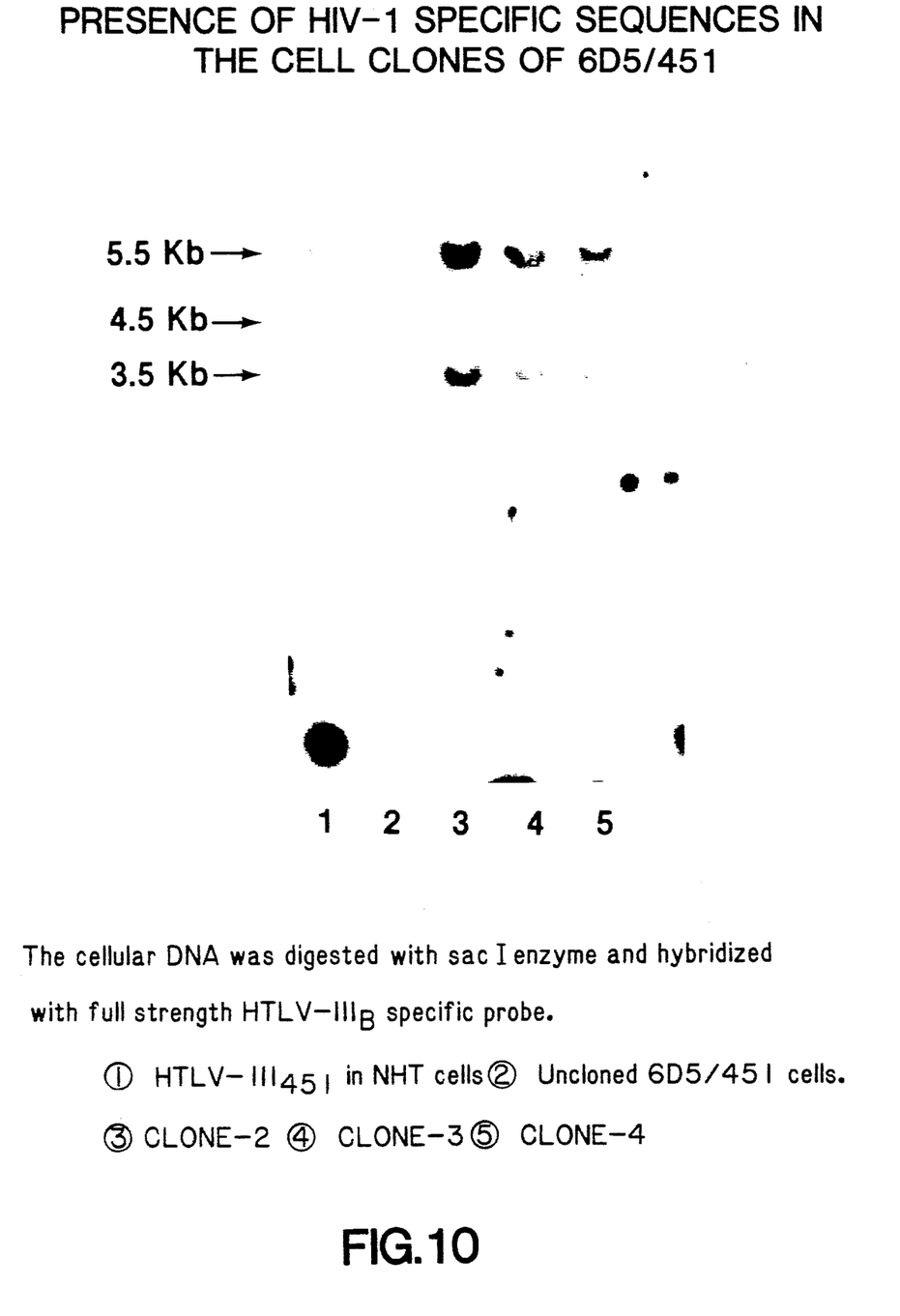
FIG. 10 shows the presence of HIV-1 sequences in 6D5$_{451}$ cell clones.

As shown in FIG. 10, the hybridizable fragments of 5.5 and 3.5 Kb were contained in all cloned cells. The clones also contained a 4.5 Kb fragment that was not present in HTLV-III$_{451}$ infected primary human T-cells.

The Southern blot analysis of the integrated provirus showed that all the cell clones harbored closely related viral genomes and that the observed differences in viral protein expression in these cells are either due to point mutations or small deletions in the viral genomes. Such genetic changes in the genome under in vitro conditions of selective pressure are to be expected in that the HIV-1 RT is known to be very highly error-prone in comparison to a number of other cellular and viral DNA polymerases (Preston et al., 1988; Roberts et al., 1988).

While particular embodiments of the invention have been described, it will be understood, of course, that the invention is not limited thereto, and that many obvious modifications and variations thereof can be made, and that such modifications are intended to fall within the scope of the appended claims.

We claim:

1. A HUT78 T-cell line infected with HTLV-III$_{451}$ having the characteristics of expressing gp160, not forming syncytia with CD4 positive cell line CEM$_{50}$, not synthesizing gag precursor protein p55, having no reverse transcriptase activity, and not producing HTLV-III virus.

2. A cell line according to claim 1 wherein said cell line is 6D5$_{451}$-clone 3, ATCC designation CRL 10307.

3. 6D5$_{451}$ cells selected from ATCC designation CRL 9946 and ATCC designation CRL 10307 in a serum-free medium.

* * * * *